United States Patent [19]

Carpenter

[11] 4,198,080
[45] Apr. 15, 1980

[54] TELESCOPING-TYPE CONNECTOR

[75] Inventor: Walter L. Carpenter, Richmond, Ill.

[73] Assignee: Baxter Travenol Laboratories, Inc., Deerfield, Ill.

[21] Appl. No.: 907,520

[22] Filed: May 19, 1978

[51] Int. Cl.$^2$ .................. F16L 27/00; F16L 37/18
[52] U.S. Cl. .................... 285/277; 24/211 L; 85/5 B; 285/316; 285/423; 403/325; 403/DIG. 6
[58] Field of Search ............. 285/316, 277, 238, 315, 285/314, 86, 84, 423; 403/322, 325, DIG. 6; 85/5 B; 24/211 R, 211 N, 211 L

[56] References Cited

U.S. PATENT DOCUMENTS

| | | |
|---|---|---|
| 3,070,393 | 12/1962 | Silverberg et al. ............ 403/325 |
| 3,188,123 | 6/1965 | Hansen ........................... 285/277 |
| 3,260,541 | 7/1966 | Sadler et al. .................. 403/325 |
| 3,334,860 | 8/1967 | Bolton, Jr. .................. 285/423 X |
| 3,551,013 | 12/1970 | Trojanowsi et al. ......... 285/316 X |
| 3,770,004 | 11/1973 | Johnson et al. ............. 285/423 X |
| 4,014,467 | 3/1977 | Ferguson .................... 285/316 X |
| 4,050,721 | 9/1977 | Streit ......................... 285/423 X |

Primary Examiner—Mervin Stein
Assistant Examiner—Carl F. Pietruszka
Attorney, Agent, or Firm—Paul C. Flattery; Garrettson Ellis

[57] ABSTRACT

A telescoping-type connector comprising outer and inner telescoping members, the inner telescoping member defining an outer circumferential groove, and adapted to sealingly fit in telescoping relation within an aperture of the outer telescoping member. The outer telescoping member includes retention means for releasably projecting into the outer circumferential groove, to retain the inner and outer members in the desired sealing, telescoping relation. In accordance with this invention, the inner telescoping member defines, between the circumferential groove and the forward end of the inner member relative to the outer member, a recessed portion on its outer surface for facilitating molding and the like. Ribbed members are positioned within the recessed portion, to prevent the retention means from projecting therein and providing inadequate locking of the connector.

2 Claims, 6 Drawing Figures

U.S. Patent Apr. 15, 1980 4,198,080
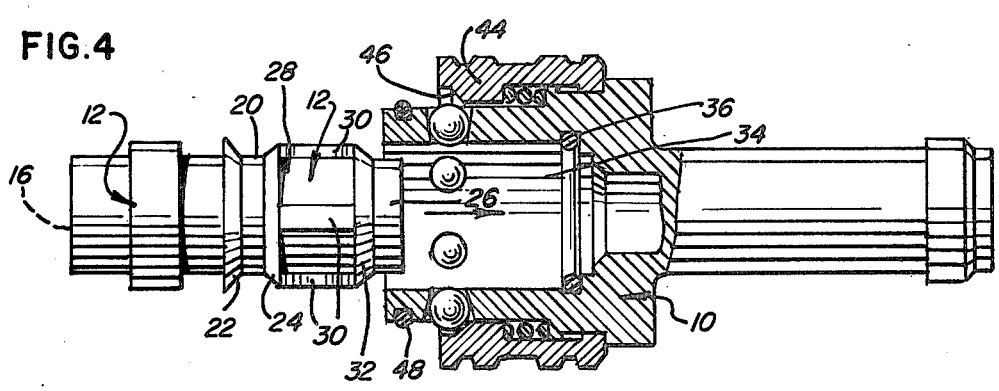
FIG. 3
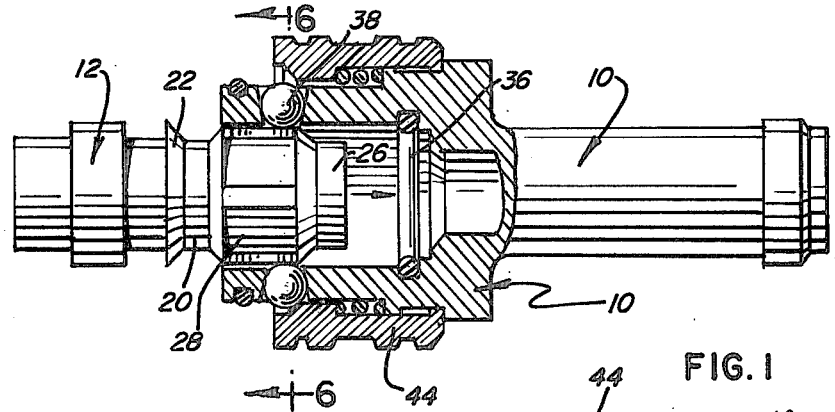
FIG. 4
FIG. 5
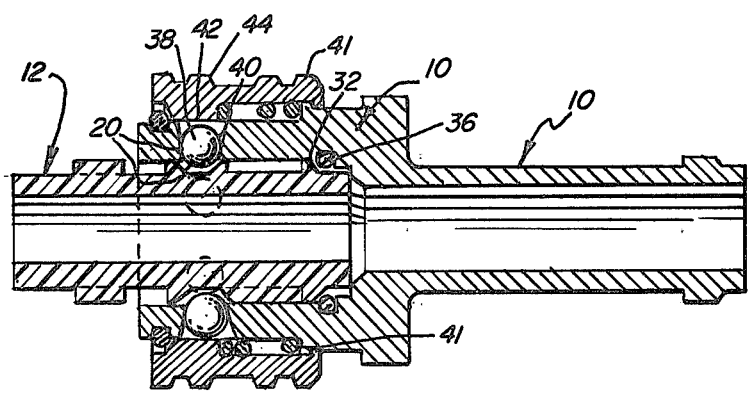
FIG. 1
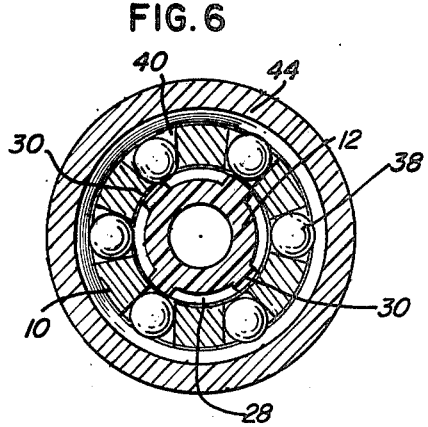
FIG. 6
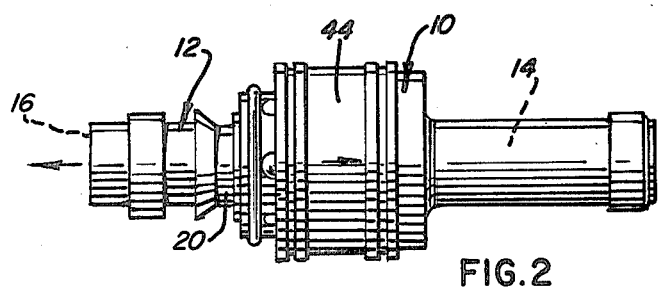
FIG. 2

TELESCOPING-TYPE CONNECTOR

BACKGROUND OF THE INVENTION

Telescoping-type connectors for fluid lines and the like are well-known, one variety of such connector being sold by the Hansen Manufacturing Company of Cleveland Ohio, known as the "Hansen Connector". Examples of such connectors are illustrated in U.S. Pat. Nos. 2,518,542; 2,761,469; 3,245,423; and 3,351,362.

A typical embodiment of this type of connector utilizes inner and outer telescoping members in which the inner telescoping member sealingly fits within an aperture of the outer telescoping member to make the desired fluid line connection. The connection is held in retention by means of several spaced, metal balls which project through the wall of the aperture of the outer telescoping member, to fit into an outer circumferential groove of the inner member for retention thereof. The balls are held in their inwardly projecting, retaining position by an outer sleeve positioned on the outer member which presses the balls inwardly. To couple and decouple the connector, the outer sleeve is axially displaced to free the balls so that they may retract outwardly, in which position the inner telescoping member may slide into or out of the outer member.

The telescoping-type connectors are suitable for use in many different fields, including the field of disposable medical devices such as dialyzers or oxygenators for blood. While in the past the telescoping-type connectors have been made of metal such as brass, stainless steel or the like, it becomes desirable in the case of disposable devices such as those mentioned above to provide a telescoping-type connector in which at least one of the telescoping members, typically the inner member, is made of an inexpensive, molded plastic, so that the connector member does not have to be salvaged following use of the disposable device.

However, it has been found that some difficulties of molding such a connector member have been encountered. For example, it is often difficult to mold the inner telescoping member of a given size, because the relatively thick section of plastic between its outer circumferential groove and its forward end, which should be of precise dimensions, is subject to warpage, distortion, and sinking as the thick section of material cools. This results in a substantial number of parts which do not meet desired manufacturing specifications because of their tendency to leak.

However, if one removes plastic from the outer portion of the thick section, a second circumferential groove can be formed which acts in a manner similar to the functioning circumferential groove intended for receiving the balls of the outer telescoping member. If the second groove does so receive the retaining balls, the connector can assume an apparently locked configuration without being actually locked in sealing condition, so that leakage takes place.

The invention of this application provides an inner telescoping member in which the thick plastic section adjacent the forward end can be reduced to save plastic, and to avoid the undesirable distortions of the dimensions which often take place in molded, thick plastic sections, while at the same time reducing the possibility of falsely locked configuration which does not seal, because the retaining balls of the outer telescoping member are projecting into the wrong area of the inner telescoping member.

Accordingly, a disposable, telescoping-type connector member is provided in which the advantages of the connector can be combined with disposable equipment.

DESCRIPTION OF THE INVENTION

In accordance with this invention, a telescoping-type connector comprises outer and inner telescoping members. The inner telescoping member defines an outer circumferential groove, and is adapted to sealingly fit in telescoping relation within an aperture of the outer telescoping member. The outer telescoping member includes retention means for releasably projecting into the outer circumferential groove of the inner member, to retain the inner and outer members in their desired sealing, telescoping relation.

In accordance with this invention, the inner telescoping member defines, between the circumferential groove and the forward end of the inner member relative to the outer member, a recessed portion on its outer surface. Rib members are positioned within the recessed portion, the rib members being positioned and proportioned to prevent the retention means from projecting into the recessed portion.

Accordingly, the desired recessed portion can be provided in the inner telescoping member to save material and weight in the inner member, and also to avoid the molding problems described above, to adapt the telescoping connector concept to inexpensive, molded plastic parts without undergoing the danger of providing a falsely locked configuration for the connector, which could permit leakage.

Preferably, the retention means are a plurality of radially arranged balls residing in the plurality of apertures in the outer telescoping member, with the balls being adapted to be pressed inwardly into retaining relation with the outer circumferential groove of the inner telescoping member by means of a sliding sleeve carried by the outer telescoping member. The sliding sleeve is spring-biased in the ball-retaining position, but can be axially moved away from the balls to allow them to be moved outwardly, to permit insertion and removal of the inner member into the outer member.

The rib members are preferably longitudinally positioned along the inner telescoping member, and do not have to equal the number of ball members present, since the connector typically cannot close if even one of the ball members is held out of position by a rib. Preferably, the ribs are so oriented that at least two ball members are held in a radially outward position at any angular relationship of the outer and inner telescoping members. Under this circumstance, the outer retaining sleeve for the ball members cannot move into its closed position, which provides a clear indication for the user that the connector is not closed.

Referring to the drawings:

FIG. 1 is an elevational view of the connector of this invention in closed and locked position.

FIG. 2 is an elevational view of the same connector of this invention, in which the outer and inner telescoping members are in telescoping but unlocked configuration.

FIG. 3 is a longitudinal sectional view of the connector in the configuration of FIG. 1.

FIG. 4 is an elevational view, taken partly in longitudinal section, showing the separated connector members about to be brought together.

FIG. 5 is an elevational view, taken partly in longitudinal section, showing the connectors in the configuration of FIG. 2.

FIG. 6 is a transverse sectional view taken along line 6—6 of FIG. 5.

Referring to the drawings, a telescoping-type connector is shown comprising outer telescoping member 10 and inner telescoping member 12. Both members define a bore 14, 16 through which fluid may pass in sealed relation through the closed connectors in the configuration of FIG. 1.

The ends 18, 20 of the respective connector members 10, 12 may be attached to appropriate tubing or to a device such as a dialyzer or oxygenator. For example, connector 10 may communicate with a conduit for dialysis solution from a dialysis solution delivery machine of conventional design, while connector member 12 communicates at its end 18 with flexible tubing leading to a dialyzer, for example a hollow fiber dialyzer, a coil dialyzer, or a plate-type dialyzer. Also, connectors 10, 12 may communicate with tubing leading between a blood oxygenator or an artificial kidney, while the other connector communicates with blood flow tubing which leads to the artery or vein of a patient. Alternatively, one or both of connector members 10, 12 may be integrally molded to the outer wall of a device such as a dialyzer or oxygenator.

Connector 12 in particular may be made of molded plastic to define an outer circumferential groove 20, which begins and terminates with longitudinally positioned angled faces 22, 24. Between outer circumferential groove 20 and the forward end 26 of inner telescoping member 12 is defined an inwardly recessed portion 28 which is crossed by ribs 30, which are of generally equal height to the radially outwardmost portions of face 24.

Ribs 30 can be seen to be parallel to each other and to extend in a longitudinal manner across recessed portion 28, and are, in the particular embodiment shown, disposed about connector 12 at 90° position angles to each other (FIG. 6), there being four ribs 30 present. However, other numbers and configurations of the ribs are contemplated to be within the scope of this invention, including annular, circumferential ribs extending about connector 12.

Adjacent the forward end 26 of inner connector member 12, an angled, annular sealing surface 32 is defined.

As shown in FIG. 3, connector member 12 can fit in telescoping relation within aperture 34 of connector member 10. In the sealed relation as shown in FIG. 3, sealing surface 32 bears against O-ring 36, which may be mounted within aperture 34, when the sealed position is achieved.

Outer connector member 10 defines an array of ball members 38 residing in pockets 40, which are open to the interior of aperture 34 as shown, and proportioned so that ball members 38 can be forced partially inwardly to aperture 34, when inner telescoping connector member 12 is properly positioned to reside in outer circumferential groove 20 so as to lock the connector. The balls are held in their locking position by sleeve 44, which is biased by spring 41 into its position in which inner surface 42 of sleeve 44 bears against the outer portion of balls 38, holding them in a radially inward position in which they project into groove 20 for sealing retention thereof.

When it is desired to either insert or remove the inner connector member 12 from the outer member 10, sleeve 44 is merely moved axially against the action of coil spring 41 until the balls 38 are released from engagement by sleeve 44. Accordingly, the balls can be cammed outwardly by sloping surface 24 when inner member 12 is being removed, or by surface 32 when inner member 12 is being inserted into the outer telescoping member 10. Then, sleeve member 44 may be released, and so that spring 40 causes sleeve 44 to resume its initial position, with balls 38 being cammed inwardly by annular bevelled surface 46. If the inner member 12 is properly positioned within the outer member 10, the balls will again reside in annular groove 20, to retain the two members together in sealed, locked configuration.

Retaining ring 48 serves to retain sleeve 46 on the rest of outer telescoping member.

Because of the presence and arrangement of ribs 30, a preferred arrangement of which is shown, it is not possible for all of the balls 38 to fall inwardly to recessed area 28 if an attempt is made to lock the connector while the balls 38 overlie that area. Accordingly, it is not possible for sleeve 44 to be biased by spring 41, in that circumstance, into its closed position overlying balls 38. As a result, the possibility of a falsely locked indication is eliminated since the partially-retracted sleeve 44, as shown in FIG. 2, provides visual indication that the device is not locked. Further retraction of sleeve 44 and an additional push of the two connector members 10, 12 together will normally provide the desired complete, sealed lock as shown in FIGS. 1 and 3.

FIGS. 5 and 6 show the configuration of the device of this invention in its telescoping but unlocked position in which ribs 30 prevent the sleeve 44 from assuming its locked position. As shown in the particular configuration, several of the balls 38 are prevented by ribs 30 from moving inwardly, although some of the balls 38 can move inwardly. This, however, is sufficient to prevent the movement of sleeve 44 into its locked configuration overlying balls 38.

As a result of the above invention, it becomes possible to make use of inexpensive, molded plastic parts, and particularly a molded plastic inner telescoping member 12, which may be attached to disposable components of a medical device such as an artificial kidney or a component of a blood oxygenator system. For example, connector 12 may be attached to the artificial kidney, an oxygenator, a cardiotomy reservoir, or the like, with a great reduction in connector expense, but no sacrifice in the reliability of operation of the sealing-telescoping member of this invention.

The above has been offered for illustrative purposes only, and is not intended to limit the invention of this application, which is as defined in the claims below.

That which is claimed is:

1. In a telescoping-type connector comprising outer and inner telescoping members, said inner telescoping member defining an outer circumferential groove and adapted to sealingly fit in telescoping relation within an aperture of the said outer telescoping member, said outer telescoping member including retention means for releasably projecting a plurality of spaced retaining members into said outer circumferential groove to retain said inner and outer members in said sealing, telescoping relation, the improvement comprising, in combination:

said inner telescoping member defining, between said circumferential grooves and the forward end of said inner member relative to said outer member, a recessed portion on its outer surface, and a plurality of circumferentially spaced, longitudinally extending rib members positioned within said recessed portion, said rib members being disposed in a position to prevent at least one of the retention members of the retention means from being projected into said recessed portion in any rotational position of said inner telescoping member while positioned within the outer telescoping member.

2. The connector of claim 1 in which four rib members are equally spaced about said inner telescoping member.

* * * * *

REEXAMINATION CERTIFICATE (191st)
United States Patent
Carpenter

[11] B1 4,198,080
[45] Certificate Issued    May 1, 1984

[54] TELESCOPING-TYPE CONNECTOR

[75] Inventor: Walter L. Carpenter, Richmond, Ill.

[73] Assignee: Baxter Travenol Laboratories, Inc., Deerfield, Ill.

Reexamination Request:
No. 90/000,320, Jan. 21, 1983

Reexamination Certificate for:
Patent No.: 4,198,080
Issued: Apr. 15, 1980
Appl. No.: 907,520
Filed: May 19, 1978

[51] Int. Cl.³ .................. F16L 27/00; F16L 37/18
[52] U.S. Cl. ........................... 285/277; 24/211 L; 285/316; 285/423; 403/325; 403/DIG. 6; 411/348
[58] Field of Search ............... 285/316, 277, 238, 315, 285/314, 86, 84, 423; 403/322, 325, DIG. 6; 24/211 R, 211 N, 211 L

[56] References Cited

U.S. PATENT DOCUMENTS

| | | | |
|---|---|---|---|
| 3,070,393 | 12/1962 | Silverberg et al. | 403/325 |
| 3,188,123 | 6/1965 | Hansen | 285/277 |
| 3,260,541 | 7/1966 | Sadler et al. | 403/325 |
| 3,334,860 | 8/1967 | Bolton, Jr. | 285/423 X |
| 3,551,013 | 12/1970 | Trojanowski et al. | 285/316 X |
| 3,731,705 | 5/1973 | Butler | 137/614.06 |
| 3,770,004 | 11/1973 | Johnson et al. | 285/423 X |
| 4,014,467 | 3/1977 | Ferguson | 285/330 X |
| 4,050,721 | 9/1977 | Streit | 285/423 X |
| 4,218,313 | 8/1980 | Aid et al. | 210/22 A |

FOREIGN PATENT DOCUMENTS

| | | |
|---|---|---|
| 1080178 | 5/1954 | France . |
| 1065269 | 4/1967 | United Kingdom . |
| 1434431 | 5/1976 | United Kingdom . |
| 1458752 | 12/1976 | United Kingdom . |

OTHER PUBLICATIONS

Plastics Engineering Handbook, 4th Ed. (Van Nostrand Reinhold Co., New York, 1976) at 153–155.
Lowell L. Scheiner, "Small Refinements Bring High Quality to Injection Tooling", Plastics Technology (May 1971) at pp. 40–42.
Plastics Engineering Handbook (Society of Plastics Industry, Inc., 3rd Ed., Reinhold Publishing Corporation, New York, 1960) at 129, 131, 286–289, 290–293 & 301–302.
Baxter Travenol advertisements: "Travenol CF TM Capillary Flow Dialyzer Model 1500" (Nov. 1976); "Travenol CF TM 1200 Capillary Flow Dialyzer" (Nov. 1977); "Travenol Setting New Standards in Negative Pressure Hemodialysis" (Oct. 1978); "CF TM Capillary Flow Dialyzers Setting New Standards in Negative Pressure Hemodialysis" (Apr. 1979).
Organon Teknika B.V. brochure: "Five Years of Organon Teknika" (see esp. pg. 7), (1977).
Organon Teknika Inc. advertisements: "Nephross performance: Now a Clear Alternative" (1979); "Nephross: The Total Fiber Environment" (1979); "Discover Just How Economical and Efficient Fluid Removal Can Be" (1979); "NEPHROSS TM Hollow Fiber Dialyzer" (1979); "NEPHROSS TM 16 F 160" (1979).
Extracorporeal Medical Specialties Inc. advertisements: "New From Extracorporeal, The TRI EX-1 TM hollow fiber dialyzer" (Mar. 1977); "What's the future look like in hollow fiber dialyzers?" (see Dialysis & Transplantation 7 (4) Apr. 1978).
Cordis Dow Corp. advertisements: "Cordis Dow C-- DAK ® 0.6 Artificial Kidney" (Nov. 1977); "Cordis Dow C-DAK TM 0.6 Artificial Kidney" (1976); "Cordis Dow C-DAK TM 1.3 Artificial Kidney" (1977); "Cordis Dow C-DAK ® 2.5 Artificial Kidney" (Nov. 1977); "Cordis Dow C-DAK ® 3500 Artificial Kidney" (1978).

*Primary Examiner*—Thomas F. Callaghan

[57] ABSTRACT

A telescoping-type connector comprising outer and inner telescoping members, the inner telescoping member defining an outer circumferential groove, and adapted to sealingly fit in telescoping relation within an aperture of the outer telescoping member. The outer telescoping member includes retention means for releasably projecting into the outer circumferential groove, to retain the inner and outer members in the desired sealing, telescoping relation. In accordance with this invention, the inner telescoping member defines, between the circumferential groove and the forward end of the inner member relative to the outer member, a recessed portion on its outer surface for facilitating molding and the like. Ribbed members are positioned within the recessed portion, to prevent the retention means from projecting therein and providing inadequate locking of the connector.

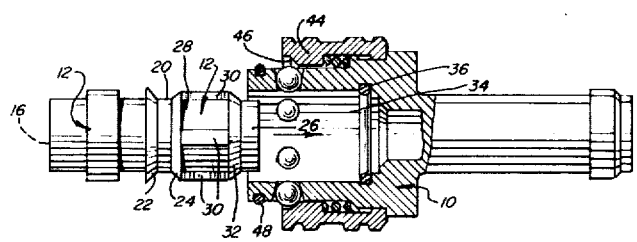

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended:

Claim 2, dependent on an amended claim, is determined to be patentable.

New claims 3 and 4 are added and determined to be patentable.

1. In a telescoping-type connector comprising outer and inner *tubular* telescoping members, said inner telescoping member defining an outer circumferential groove and adapted to sealingly fit in telescoping relation within an aperture of the said outer telescoping member, said outer telescoping member including retention means for releasably projecting a plurality of spaced retaining members into said outer circumferential groove to retain said inner and outer members in sealing, telescoping relation, the improvement comprising, in combination:

said inner telescoping member defining, between said circumferential [grooves] *groove* and the forward end of said inner member relative to said outer member, a recessed portion on its outer surface, and a plurality of circumferentially spaced, longitudinally extending rib members positioned within said recessed portion, said rib members being disposed in a position to prevent at least one of the [retention] *retaining* members of the retention means from being projected into said recessed portion in any rotational position of said inner telescoping member while positioned within the outer telescoping member, *the area occupied by said rib members in the recessed portion being less than the remaining area of said recessed portion which is free of said rib members.*

3. *The connector of claim 1 in which said inner telescoping member is made of molded plastic.*

4. *The connector of claim 1 in which areas of said recessed portion free of said rib members are large enough to receive individual retaining members.*

* * * * *